United States Patent [19]

Schwartz

[11] Patent Number: 4,775,369

[45] Date of Patent: Oct. 4, 1988

[54] AUTOMATICALLY ACTIONABLE SHARPENED NEEDLE-TIP PROTECTION

[76] Inventor: Boris Schwartz, 625 Lafayette Ave., Hawthorne, N.J. 07506

[21] Appl. No.: 57,486

[22] Filed: Jun. 3, 1987

Related U.S. Application Data

[63] Continuation-in-part of Ser. No. 905,196, Sep. 9, 1986, abandoned.

[51] Int. Cl.$^4$ .............................................. A61M 5/32
[52] U.S. Cl. .................................... 604/263; 604/198
[58] Field of Search ................................. 604/192–198, 604/263, 162, 411–414

[56] References Cited

U.S. PATENT DOCUMENTS

| | | | |
|---|---|---|---|
| 2,847,995 | 8/1958 | Adams | 604/263 X |
| 3,134,380 | 5/1964 | Armao | 604/198 |
| 3,380,448 | 4/1968 | Sadove | 604/263 |

FOREIGN PATENT DOCUMENTS

| | | | |
|---|---|---|---|
| 1203065 | 1/1960 | France | 604/411 |

Primary Examiner—Dalton L. Truluck
Attorney, Agent, or Firm—Ralph R. Roberts; Patrick J. Pinto

[57] ABSTRACT

This invention provides a protector for a sharpened tip of a needle of conventional construction. Preferably, foam rubber or plastic is used, with the rear of this foam material secured to the hub containing the needle and with the fore end of the foam material secured to a molded tubular guide end member. An inner sleeve is provided with the foam material. This foam material is shown as an extrusion or as a strip with adhesive on one side. This protector is accordionized when the needle is advanced into the patient. Bias may also be provided by a spring. The spring is shown as an integral part of a tubular length, with the interstice portions extending between convolutions of the spring. Three embodiments of spring placement are shown. In all embodiments, it is anticipated that the needle and protector will be brought to the patient, and with the needle advancement the protector accordionizes as the needle is inserted. The bias moves the end member to a tip-protecting condition and position as the needle is withdrawn.

10 Claims, 3 Drawing Sheets

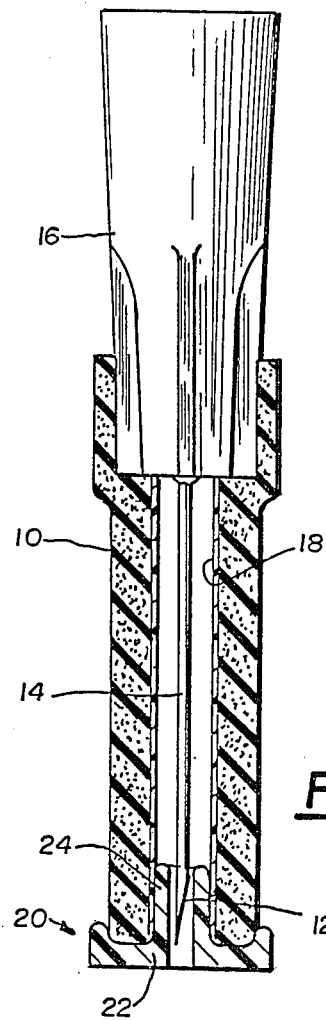
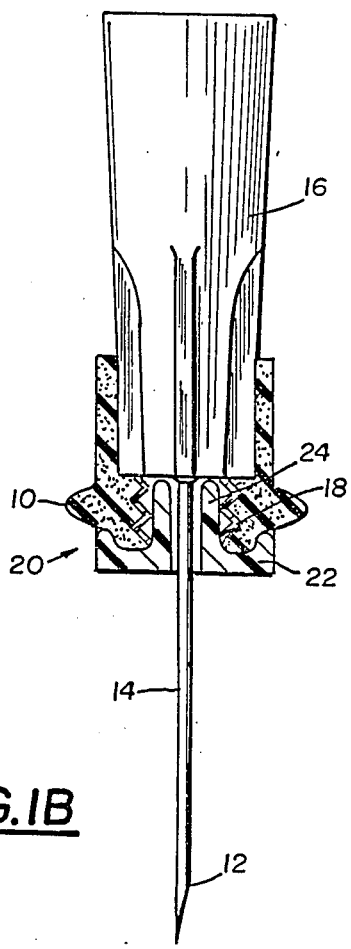
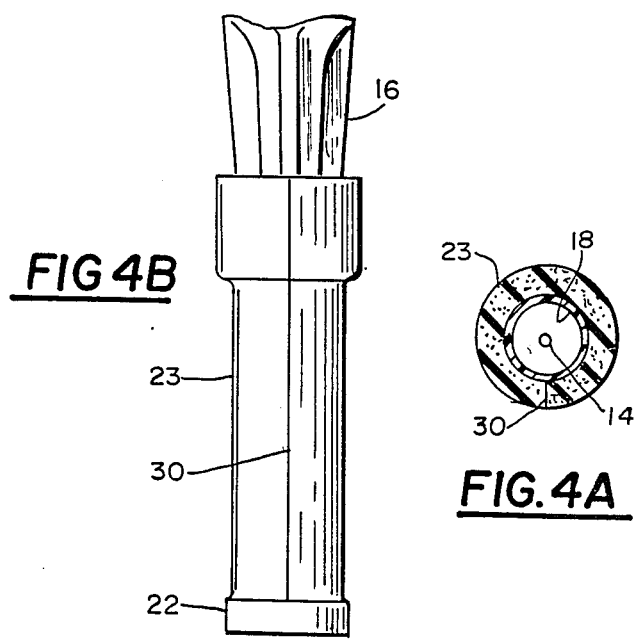
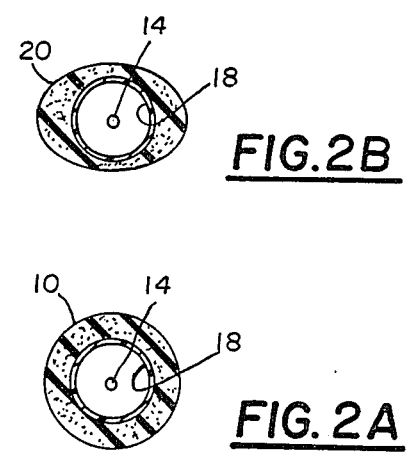
FIG.1B  FIG.1A  FIG.4B  FIG.4A  FIG.2B  FIG.2A

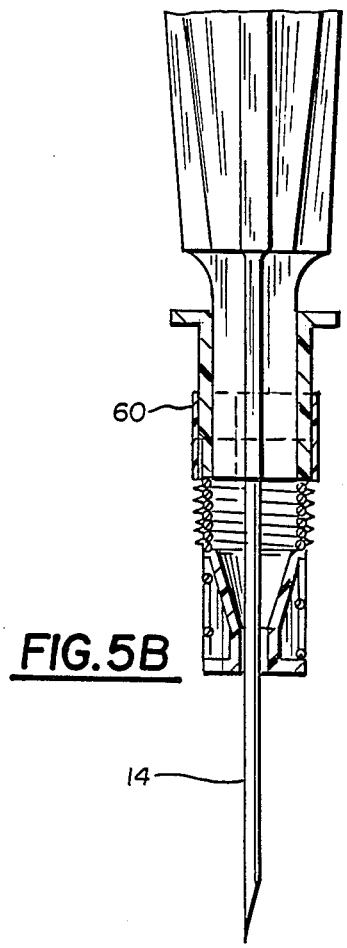
FIG.5B
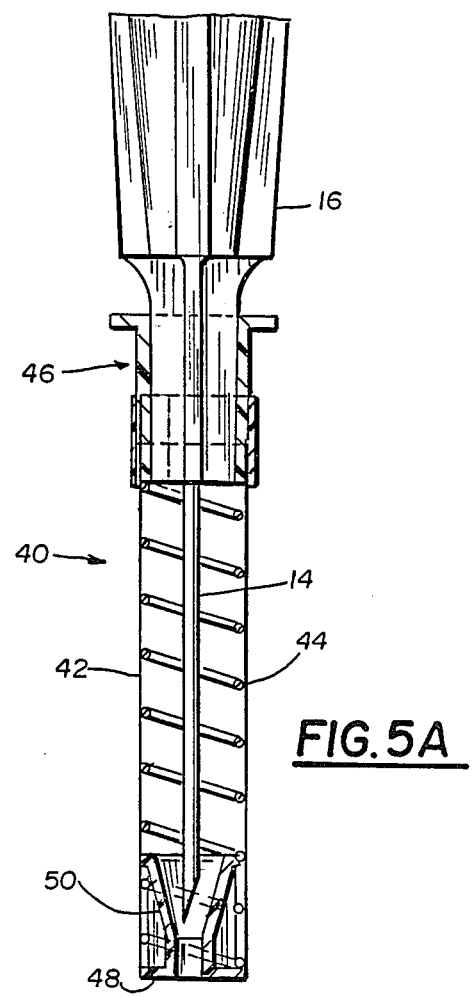
FIG.5A
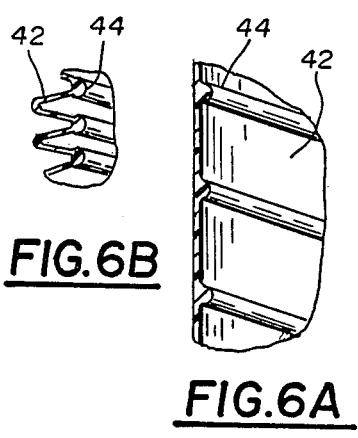
FIG.6A
FIG.6B
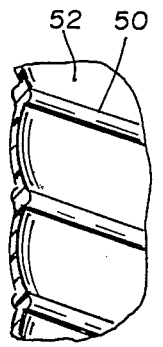
FIG.6C
FIG.6D
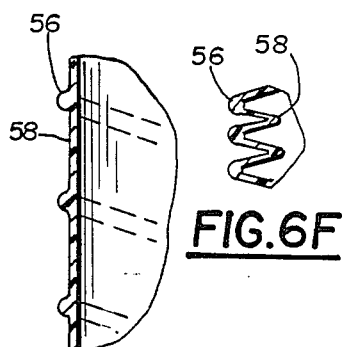
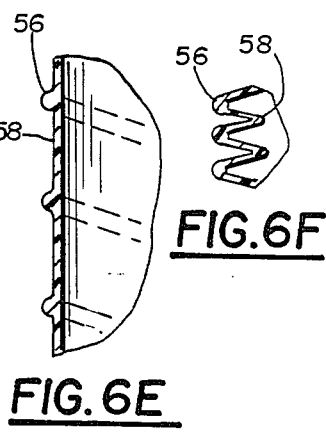
FIG.6E
FIG.6F

AUTOMATICALLY ACTIONABLE SHARPENED NEEDLE-TIP PROTECTION

CROSS REFERENCE TO APPLICATION

This is a C-I-P Application of my prior application having the same title and having Ser. No. 905,196, as filed Sept. 9, 1986. Election was made on Feb. 13, 1987. With the acceptance of this Application, the prior Application Ser. No. 905,196 is expressly abandoned.

BACKGROUND OF THE INVENTION

1. Field of the Invention

The field of invention as established in and by the U.S. Patent Office is believed to be in the general class entitled "Surgery" and in the subclass pertaining to syringes used to introduce and remove liquid material from a body. More particularly, this invention is directed to a cover or protector of the sharpened tip of a needle in which the protector is moved in response to the advancing insertion and withdrawal of the needle into a patient.

2. Description of the Prior Art

The covering of the sharpened tip end of a needle to protect the attendant has been the subject of many patents extending back for more than thirty years. Among these patents are: U.S. Pat. No. 2,876,770 to WHITE as issued on Mar. 10, 1959. Also noted are: U.S. Pat. No. 2,925,083 as issued to CRAIG on Feb. 16, 1960; U.S. Pat. No. 3,040,743 as issued to NAESS on June 26, 1962; U.S. Pat. No. 3,306,290 issued to WELTMAN on Feb. 28, 1967; U.S. Pat. No. 3,406,687 as issued to MOYER on Oct. 22, 1968, and U.S. Pat. No. 4,425,120 as issued to SAMPSON et al on Jan. 10, 1984. These patented devices propose to provide a tip protector that prevents exposure after use.

At present, a molded cap or thimble is placed on each of the needles used with syringes. These caps prevent accidental pricking of the needle into an adjacent member. When and after the needle is exposed with removal of this cap, the sharp end is and remains exposed. Prior to the advent of Hepatitis and AIDS, the worry of the attendant was a prick, which may or may not have been uncomfortable. With the danger of infection from Hepatitis and AIDS, protection from a prick or penetration by the sharpened tip is mandatory.

The patent to WHITE utilizes a rigid shield with a spring urging the shield to its outward condition. Manual manipulation and a bayonet-type lock are also employed to maintain the shield in a retracted condition. CRAIG also provides a rigid shield and a spring. When the shield of CRAIG is moved to needle-exposed condition, a latch is utilized to release the shield. WELTMAN builds the rigid needle protector into the syringe housing, with the needle and syringe a reusable product. These patents show needle protectors with spring means, but all are expensive and contemplate rigid shield members. The present invention is adapted for use with the disposable syringes now used and with the sharp needle tip being protected immediately, when withdrawal from the patient is made.

SUMMARY OF THE INVENTION

This invention may be summarized, at least in part, with reference to its objects. It is an object of this invention to provide, and it does provide, a needle-tip protector for a sharpened needle carried on a disposable syringe or blood aspirator. This protector has an end portion movable against lightly applied pressure needed to insert the needle in a patient. This pressure is sufficient to maintain this end against the patient during use and sufficient to move this protector to and past the sharpened tip of the needle as withdrawal is made so that the sharpened tip is covered against unwanted and accidental penetration.

It is a further object of this invention to provide, and it does provide, a needle protector in which a molded end member is formed to slide on the shank of a needle, with this end member urged to its outer condition by self-contained bias pressure, and with means to establish the outer limit positioning of the protective end.

In brief, the invention to be described in detail hereinafter includes a needle which is mounted to and in a hub that is mountable on a disposable syringe of conventional construction. In the mounted condition and with the protector in place, the sharpened tip of the needle does not extend to the end of the protector. The protector has a tubular guide portion sized to be freely slideable on the shank of the needle. A bias force is provided so that the molded end of the protector is at an extending limit which insures that the protector extends to a determined limit. The protector is secured to the hub holding the needle.

In one embodiment, a foam plastic or rubber extrusion provides the bias force. A very thin, plastic tubular liner is provided in one embodiment. The foam extrusion and liner accordionizes to provide a small space. This extrusion may be a round tube or may have an oval or irregular configuration. Foam rubber may be utilized in sheet form and with applied adhesive assembled to a thin flexible tube and molded end member to provide an inexpensive enclosure. The protector is also shown with a spring-like molding in which the molding is integral with the intermediate portions. The rear of this protector may have a molding adapted to be secured to a syringe or may utilize an adhesive strip. The integral molding depicts the spring component in three arrangements.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of an automatically actionable sharpened needle protector as adopted for use with a conventional hypodermic syringe or blood aspirator and showing a preferred means for covering the sharpened tip of the needle. This specific embodiment and alternates thereof have been chosen for the purposes of illustration and description as shown in the accompanying drawings wherein:

BRIEF DESCRIPTION OF THE DRAWINGS

FIGS. 1 A and 1 B represent side sectional views, partly diagrammatic, and showing a needle-tip protector secured to a syringe hub, FIG. 1 A representing the protector in extended condition and FIG. 1 B representing the protector in compressed and in a needle tip-exposed condition;

FIGS. 2 A and 2 B represent sectional views of the extruded foam of FIG. 1 A and illustrate round and oval extrusion configurations with the liner in place;

FIGS. 4 A and 4 B represent sectional and diagrammatic side views of a needle protector made in accordance with the assembly method shown in FIG. 3;

FIGS. 5 A and 5 B represent side sectional views, partly diagrammatic, and showing a needle point protector utilizing a spring as a bias, the spring molded integrally with thin, flexible interstice portions, FIG. 5 A representing the needle protector in the expanded condition and FIG. 5 B representing the device of FIG. 5 A with the molded spring portion in a compressed condition;

FIGS. 6 A, 6 B, 6 C, 6 D, 6 E, and 6 F represent sectional views, greatly enlarged and fragmentary, to illustrate the integral molding of the needle sheath with spring bias means, FIG. 6 A representing a molding in which the spring portion is arrayed to the interior, FIG. 6 B represents the molded portion of FIG. 6 A and with the protector compressed to provide accordionizing of the intermediate web of the molded portion, FIG. 6 C represents the needle sheath portion similar to FIG. 6 A, but with the spring portion intermediate the web portion, FIG. 6 D represents the molded portion of 6 C, but in a compressed condition as in 6 B, FIG. 6 E represents the molded portion similar to FIG. 6 A, but with the spring portion exterior of the intermediate web portion, and FIG. 6 F represents the molded portion of FIG. 6 E, but in the compressed condition.

In the following description and in the claims, various details are identified by specific names for convenience. These names are intended to be generic in their application. Corresponding reference characters refer to like members throughout the several figures of the drawings.

Figure 3:
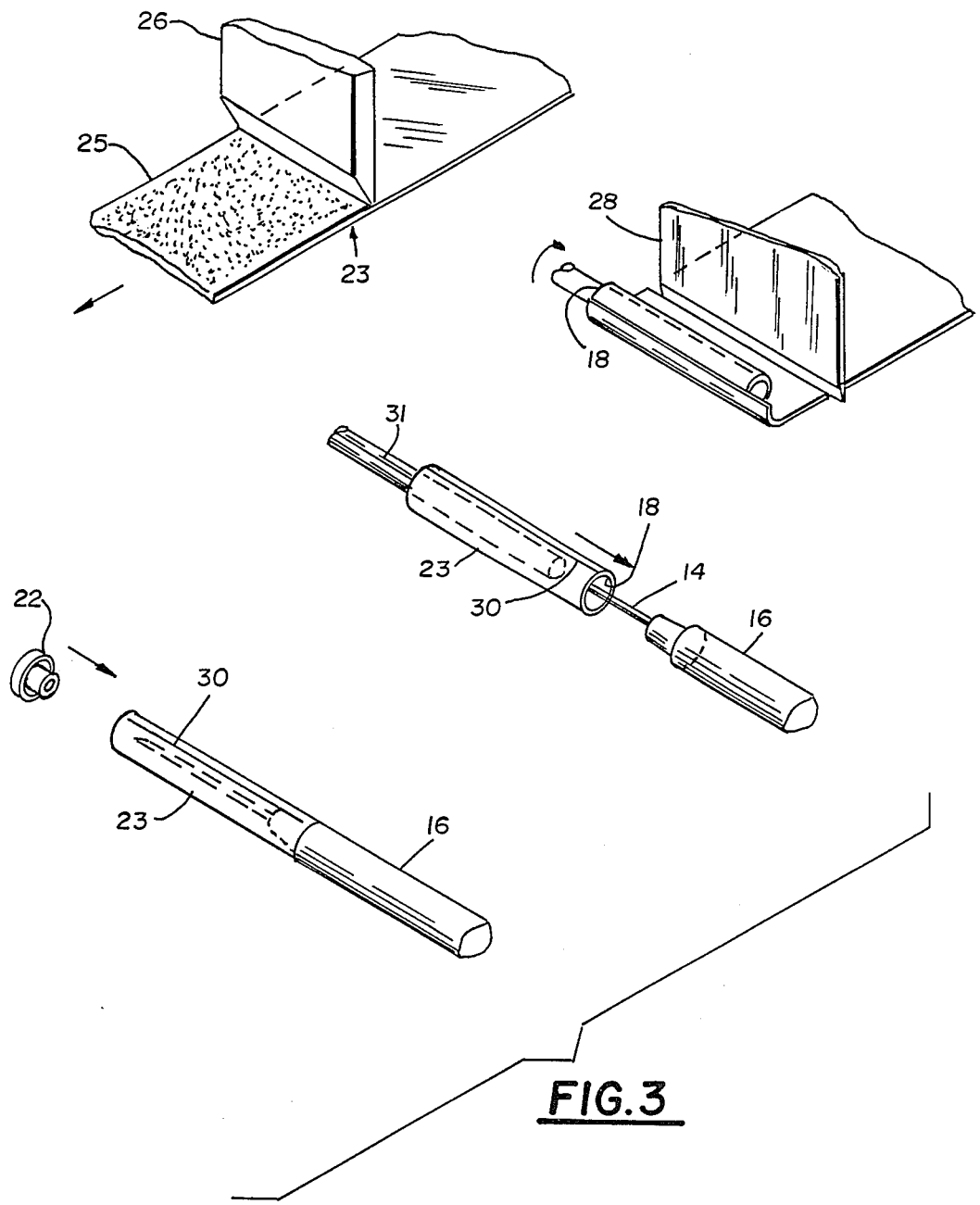
FIG. 3 represents an exploded isometric view, partly diagrammatic, and showing a method of making and assembling a compressible foam rubber member for use with and on a syringe.

The drawings accompanying, and forming part of, this specification disclose details of construction for the purpose of explanation, but structural details may be modified without departure from the concept and principles of the invention and the invention may be incorporated in other structural forms than shown.

NEEDLE-TIP PROTECTOR AS SHOWN IN FIGS. 1 A AND 1 B

FIGS. 1 A and 1 B diagrammatically show the needle-tip protector of this invention, utilizing an extruded foam member 10 of rubber or plastic. This protector is used to protect and cover a sharpened tip 12 of a needle 14 of conventional construction. This needle is conventionally secured to a hub 16 which may be integral with or secured to a disposable syringe. As depicted in FIG. 1 A, the extrusion 10 also includes a thin, plastic tubing liner 18 which extends from the hub 16 to the front or fore end of the extrusion. A molded plastic end member, generally identified as 20, has a face portion 22 and a hollow tubular guide portion 24 adapted and sized to freely slide on and along the shank of the needle 14.

EXTRUSION SHAPE AS IN FIGS. 2 A AND 2 B

The extrusion product as shown in FIGS. 1 A and 1 B may have a selected cross-sectional configuration. In FIG. 2 A, the extrusion is shown as round, which is conventional. In FIG. 2 B, the extrusion is depicted as having an oval configuration which, for purpose of identification, is identified as 20. As conventionally extruded, an aperture sized to receive tube 18 is provided. This aperture is sized to suit a particular condition.

ASSEMBLY USING FOAM SHEETING AS IN FIG. 3

In FIG. 3 there is depicted an inexpensive means for making and assembling a foam rubber compression portion. This method contemplates utilizing sheet material rather than extruded materials. Often it is very desirable to utilize silicone rubber as foam material. Silicone foam rubber is difficult to extrude, but is available in sheet form. Silicone rubber that is impervious to fluids and the like is selected so the adverse effect of wetting of the foam is avoided. A strip of silicone foam 23 has one (upper) surface coated with adhesive 25, which may be diagrammatically applied in a desired thickness by applicator 26. After coating, a tube 18 of determined size and length is provided. This tube is of thin plastic and is rotated as indicated so that the adhesive side 25 of the foam strip 23 is brought in engagement with said tube. A knife 28, or like cutting means, longitudinally severs this foam so that the foam material just makes a wrap (circumference) around the tube 18.

The wrap of material around tube 18 is anticipated to leave a very small joint 30 in the final product. A pushing device 31 is suggested so as to push the foam wrap 23 and tube 18 to and on the front end of syringe 16. The needle 14 is already in position. A molding end 22, which is identical to or similar to that shown in FIG. 1 A, is inserted into the end of the wrap of foam 23. Assembly is contemplated to be by automatic machinery.

USE AND OPERATION

The needle-tip protector as shown and described above is easily and economically made. Assuming the structure of FIGS. 1 A and 2 B, a mandrel of assembly (not shown), receives and retains a length of tubing liner 10 and then the plastic end member 20 is positioned within or adjacent this liner. The extrusion 10 is cut to length and end member 20 is inserted in tube 18. The syringe with needle attached is now advanced, and with expanding and guiding finger means the tubing 10 is caused to be stretched to slide a short distance on the fore portion of the hub 16. In the expanded condition, the needle tip 12 is protected and, when it is desired to use the syringe and needle 14, this end 20 and front seal 26 are brought to and contiguous to the prepped skin of a patient. In use, the needle 14 is pushed forwardly, with the sharp tip end 12 penetrating and entering the patient. After the usual withdrawal of blood or injection, the needle 14 is withdrawn. The foam extrusion 10 is adapted to compress so that the tubular guide 24 of end member 20 is adjacent the hub 16. As this illustration is in a greatly enlarged scale, the arrangement of FIG. 1 B anticipates the needle to be exposed except for about one-eight of an inch. If the penetration required is less, then the end member and tubular guide 24 will be partially along the needle 14. The liner 18 is used so that friction from the foam extrusion 10 does not and cannot restrict the return of the protector device to cover the tip 12 of the needle 14. It is important that the tip 12 of the needle be covered after use to provide protection from the possible puncture and exposure of the attendant to hepatitis or AIDS from the blood of the patient.

The assembly of the foam rubber protector having sheet construction as in FIGS. 3, 4 A and 4 B has been discussed above. In use, it is anticipated that the foam rubber 23 is of sufficient thickness and bias to be compressed similar to the showing in FIG. 1 B, but also to expand thereafter to cover the sharp end 12 of the needle 14. It is, of course, realized that the drawings are in a greatly enlarged scale for the purpose of clarification.

PROTECTOR AS IN FIGS. 4 A AND 4 B

The foam rubber protector, as shown in FIG. 3, is depicted in FIG. 4 A in which needle 14, tube 18, foam material 23 are represented in relaxed condition. The foam material has been wrapped around tube 18 so that a very small joint 30 is formed. In FIG. 4 B, the protector is illustrated in a side elevation. As seen, the forward end of the needle hub 16 has the adhesive side of the foam strip 23 secured to this hub. The foam 23 has the split 30 extending to the forward molded guide 22. If desired, the foam material 23 and tube 18 may terminate at the same point and an adhesive strip be utilized for securement.

PROTECTOR EMBODIMENT OF FIGS. 5 A AND 5 B

In FIGS. 5 A and 5 B is illustrated a needle protector utilizing a mid-portion which is a molding. Conventionally, this is of a plastic having sufficient bias so that a spring portion is a unitary component of this molding. The hub 16 and the needle 14 are like that in FIG. 1 A, but instead of a tube 18, there is provided a molding, generally identified as 40. This molding includes an interstice portion 42, which is sufficiently supple so as to be accordionized. A spring portion 44 is formed as this is molded. This spring portion provides the needed bias to urge the protector to an expanded position and condition. For ease of mounting of the hub 16, there is provided a tubular connector 46 which is adapted for removable securement to said hub. At the distal end of the molding, there is provided another rigid molding 48, which is depicted as having a conical guide 50 for the sharp end of the needle 14. In FIG. 5 B is illustrated that portion between connector 46 and end 48 in an accordionized condition and with needle 14 in exposed condition. It is to be noted that this molding 40 is contemplated to be molded with the springs in a selected position.

ENLARGED SHOWING OF FIGS. 6 A, 6 B, 6 C, 6 D, 6 E, and 6 F

In FIGS. 6 A and 6 B, the molding of FIG. 5 A is repeated, with the spring portion 44 disposed interior of the interstice portion 42. In an accordionized condition (compressed) as in FIG. 6 B, the interstice portion 42 bulges outwardly and occupies that portion between adjacent coils of the spring portion.

In FIGS. 6 C and 6 D, the molding, generally identified as 40, has the spring portion (identified as 50) midway of the connecting interstices 52. Although shown substantially mid-portion, this does not preclude other mid-portion placement. This molding, like the showing of FIG. 5 A, is intended to extend from connector 46 to the distal end of member 48. In a compressed condition as in FIG. 6 D, the interstice portion 52 bulges outwardly and the spring portions 50 are adjacent each other.

In FIGS. 6 E and 6 F, the molding, generally identified as 40, has the spring portion identified as 56 exteriorally positioned. Between spring portions are interstice portions 58. The interstice portions 58 are preferably directed inwardly to allow the spring portions to be adjacent each other. The accordionized condition is depicted in FIG. 6 F.

In the embodiments of FIGS. 5 A through 6 F, the needle protector employs the tube and spring molding 40 to provide the needed and desired movable and compressible sleeve. Retention to the hub 16 may be directly by an adhesive band or strip 60, in which condition the needle 14, hub 16 and associated components are discarded with the syringe. If tubular connector 46 is present and employed, the adhesive band 60 is used to retain the molding portion 40 to this connector 46. The distal end member 48 is depicted as inserted within the molded portion 40. The desired configuration of the molding 40 is considered in the forming of the molding of this distal end member 48.

The several embodiments and/or variations of the sharpened tip needle protector anticipate an inviolate side extent adapted to prevent unwanted contamination of the needle. Where extruded material is used as the bias force, the foam extrusion is sufficiently dense to provide this protection. The foam extrusion is locally stretched so as to tightly grip the needle hub. The end member 20 is of a plastic material that is freely slideable on and along the needle shank.

The showing of FIGS. 3 through 4 B also uses foam rubber over a plastic tube to provide a barrier to the passage of air to the needle. Bias is provided by the foam rubber sheet. The molding of plastic with integral spring means, as found in FIGS. 5 A through 6 F, also provides a barrier to the passage of air and the like.

In the several embodiments, it is contemplated that the movable end member has a defined and established tip-protector limitation. When a foam extrusion is used, the relaxed condition provides this outer sharpened tip protection. As the use of the needle in the patient is for only a few minutes, the foam extrusion does not have time to take a set. When and where a molded spring provides the bias, it is anticipated that the molded member establishes and provides a determined outward limit of movement. This molded section is secured to both the outer end and the retainer molding which is configured to provide a determined snug and excluding fit to the hub of the needle. The outer configuration of the extrusion is shown as round or oval, but other shapes may be provided-and particularly irregular shapes. Extrusions are subject to manufacturing problems so precise limitations on configuration are not contemplated. Adhesive, solvent-sealing, sonic welding, etc., are contemplated as means for insuring retention of the front end member 20 to the extrusion 10. Adhesive securement means is contemplated to retain the flexible foam rubber strip to the front molding and to the needle hub. Extruded and strip foam and spring provide the bias and all are contemplated to have a ratio of compression such as at least five to one.

The above-disclosed embodiments also suggest and provide a method of constructing a needle-tip protector. These embodiments illustrate steps of construction and use as follows: providing a front-end tubular guide member and forming in said member an inner through passageway sized to be freely slideable on and along a shank portion of a sharpened needle;

-urging the front-end tubular guide member by bias means to a determined tip-protecting position which is a short distance beyond the sharpened tip;
-securing said protective member assembly to that hub carrying and retaining said needle, and
-arraying barrier so as to extend between the needle hub and said front-end tubular guide member.

Terms such as "left," "right," "up," "down," "bottom," "top," "front," "back," "in," "out" and the like, are applicable to the embodiments shown and described in conjunction with the drawings. These terms are merely for the purposes of description and do not necessarily apply to the position in which the sharpened needle-tip protector may be constructed or used.

While particular embodiments of the needle-tip protector have been shown and described, it is to be understood that the invention is not limited thereto and protection is sought to the broadest extent the prior art allows.

What is claimed is:

1. A sharpened needle-tip protector for a conventional needle secured to and mounted in a hub which is adapted for mounting on the discharge end of a syringe, said tip protector adapted to be moved along a shank of said needle as the needle is inserted and advanced into a patient, the tip protector movable against a self-contained bias so that as the needle is withdrawn from the patient, the tip protector is urged by the bias to its original tip-protecting position whereby the sharpened tip of the needle is again covered so as to prevent accidental pricking of the attendant, said sharpened needle-tip protector including:
   (a) a front-end tubular guide member having an inner through passageway sized to be freely slideable on and along the shank portion of said sharpened needle;
   (b) said bias means is provided by an extrusion of foam material having an internal bore and an external configuration having a resiliency and a compressive capability of at least five to one, the foam being sufficiently dense so as to provide an inviolate barrier to external contamination;
   (c) said internal bore of the extrusion being arrayed over a determined length of thin flexible liner having a low coefficient of friction so as to provide a sliding surface adjacent the shank of the sharpened needle;
   (d) means for securing said protective member to that hub carrying and retaining said needle, and
   (e) said inviolate barrier extending between the needle hub and said front-end tubular member, this barrier maintaining exclusion of air during and until time of use.

2. A sharpened needle-tip protector as in claim 1 in which the front-end tubular guide member is a plastic molding having a recess sized and adapted to seat and retain the front end of said extrusion and with said molding havings its external-end surface disposed so as to be substantially normal to the axis of the needle.

3. A sharpened needle-tip protector as in claim 1 in which the bias means is provided by a strip of resilient foam material wrapped in a tube configuration around a liner tube, this foam material having a resiliency and a compressive capability of at least five to one, the foam material being sufficiently dense so as to provide a barrier to external contamination.

4. A sharpened needle-tip protector as in claim 3 in which the tube is a thin, flexible liner having a low coefficient of friction so as to provide a sliding surface adjacent the shank of the needle.

5. A sharpened needle-tip protector as in claim 4 in which the foam rubber strip has one surface coated with adhesive and has this adhesive surface brought to and in contact with the outer surface of said tube so that a full wrap of the strip around said tube is made, and said tube is made sufficiently shorter than the foam strip so that this adhesive surface of the strip is utilized to engage and retain the front-end tubular guide member.

6. A sharpened needle-tip protector as in claim 5 in which the foam rubber strip and the adhesive coating thereon are made so as to extend to the rear of and beyond the tube so that this rearwardly-extending portion and the adhesive surface thereon are sufficient to provide a desired securing means for attachment of the needle-tip protector to the hub of the needle.

7. A method of constructing, assembling and using a sharpened needle-tip protector for a conventional needle secured to and mounted in a hub adapted for mounting on the discharge end of a syringe, the tip protector movable against a self-contained bias so that as the needle is withdrawn from the patient, this tip protector is moved by the bias to its tip-protecting position and preventing accidental pricking of the attendant, said steps including:
   (a) providing a front-end tubular guide member and forming in said guide member an inner through passageway sized to be freely slideable on and along a shank portion of a sharpened needle;
   (b) providing a bias means by and of an extrusion of foam material having an internal bore and an external configuration and having a resiliency and compressive capability of at least five to one;
   (c) providing a thin flexible tubular barrier so as to extend between the needle hub and said front end tubular guide member, this tubular member adjacent the shank of the needle;
   (d) arraying said thin flexible tubular member in the bore of said extrusion so as to provide a sliding surface and having a low coefficient of friction on and with the shank of the needle; and
   (e) securing said protective member assembly to that hub carrying and retaining said needle.

8. A method of constructing and assembling a sharpened needle-tip protector as in claim 7 which includes forming the front-end tubular guide member as a plastic molded member having a recess in one face.

9. A method of constructing and assembling a sharpened needle-tip protector as in claim 7 which includes providing the bias as a foam rubber strip and coating one side of said strip with adhesive, and supplying a thin, flexible tubular liner in the bore of the extrusion so as to provide a sliding surface having a low coefficient of friction, this tubular liner adjacent the shank of the needle, and wrapping this adhesive-coated strip of foam to and around said tube and the front-end tubular guide member.

10. A method of constructing and assembling a sharpened needle-tip protector as in claim 9 which includes forming the adhesively-coated foam material of a length sufficient to extend rearwardly beyond the tubular liner so that this rearwardly-extending foam material may be and is secured by the adhesive to the hub of the needle.

* * * * *